(12) United States Patent
Ikonomidou et al.

(10) Patent No.: US 7,232,813 B2
(45) Date of Patent: Jun. 19, 2007

(54) NEUTRAL ENDOPEPTIDASE (NEP) AND HUMAN SOLUBLE ENDOPEPTIDASE (HSEP) INHIBITORS FOR PROPHYLAXIS AND TREATMENT OF NEURO-DEGENERATIVE DISORDERS

(75) Inventors: Hrissanthi Ikonomidou, Weesp (NL); Lechoslaw A. Turski, Weesp (NL); Dieter Ziegler, Weesp (NL); Michael Weske, Weesp (NL)

(73) Assignee: Solvay Pharmaceuticals B.V., Weesp, Holland ( * ) Notice: Subject to any disclaimer, the term of this patent is extended or adjusted under 35 U.S.C. 154(b) by 183 days.

(21) Appl. No.: 11/030,043

(22) Filed: Jan. 7, 2005

(65) Prior Publication Data

US 2005/0153936 A1  Jul. 14, 2005

Related U.S. Application Data

(60) Provisional application No. 60/535,538, filed on Jan. 12, 2004.

(51) Int. Cl.
*A61P 25/00* (2006.01)

(52) U.S. Cl. ............... 514/211.06; 514/212.07
(58) Field of Classification Search .......... 540/487, 540/491, 523; 514/211.06, 212.07
See application file for complete search history.

(56) References Cited

U.S. PATENT DOCUMENTS

| 5,677,297 | A | 10/1997 | Waldeck et al. |
| 5,952,327 | A | 9/1999 | Waldeck et al. |
| 2002/0013307 | A1 | 1/2002 | Lapuerta et al. |

FOREIGN PATENT DOCUMENTS

| WO | WO 02/094176 | 11/2002 |
| WO | WO 2004/082637 A | 9/2004 |

OTHER PUBLICATIONS

Tabrizchi, R., "Current Opinion in Investigational Drugs," Pharmapress, 4(3):329-332 (2003).

*Primary Examiner*—Bruck Kifle
(74) *Attorney, Agent, or Firm*—Finnegan, Henderson, Farabow, Garrett & Dunner, L.L.P.

(57) ABSTRACT

The invention relates to a novel use of known benzazepine, benzoxazepine, benzo-thiazepine-N-acetic acid and phosphono-substituted benzazepinone derivatives having neutral endopeptidase (NEP) and/or human soluble endopeptidase (hSEP) inhibitory activity. The compounds of the invention are useful for the preparation of pharmaceutical compositions for prophylaxis and treatment of neuro-degenerative disorders.

The compounds of the invention are known from the European patents EP 0 733 642 and EP 0 916 679, and can be described by the general formulae (1):

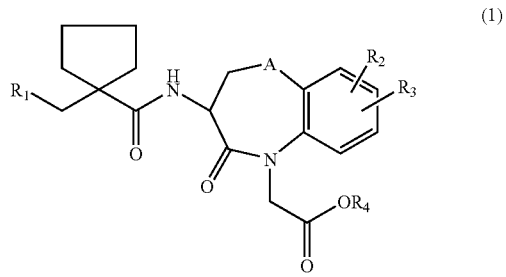

wherein the symbols have the meanings as given above in the description.

11 Claims, No Drawings

NEUTRAL ENDOPEPTIDASE (NEP) AND HUMAN SOLUBLE ENDOPEPTIDASE (HSEP) INHIBITORS FOR PROPHYLAXIS AND TREATMENT OF NEURO-DEGENERATIVE DISORDERS

CROSS REFERENCE TO RELATED APPLICATION

This application claims the benefit of U.S. Provisional Application Ser. No. 60/535,538, filed Jan. 12, 2004, the content of which is incorporated herein by reference.

The invention relates to a novel use of known benzazepine, benzoxazepine, benzo-thiazepine-N-acetic acid and phosphono-substituted benzazepinone derivatives having neutral endopeptidase (NEP) and/or human soluble endopeptidase (hSEP) inhibitory activity. The compounds of the invention are useful for the preparation of pharmaceutical compositions for prophylaxis and treatment of neurodegenerative disorders The invention relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament.

In patent application US 20030045449 it is described that matrix-metalloprotease inhibitors are useful for the treatment of neurodegenerative disorders. Problems associated with that invention are first that matrix-metalloprotease inhibitors comprise a broad group of protease inhibitors, and second that according to the said application the metalloproteases must be used in a pharmaceutical composition also containing a N—NOS inhibitor.

The goal of the present invention was to identify specific metalloprotease inhibitors which are of therapeutic value when administered as monotherapy.

Surprisingly, it now has been found that benzazepine, benzoxazepine, benzothia-zepine-N-acetic acid and phosphono-substituted benzazepinone derivatives having neutral endopeptidase (NEP) and/or human soluble endopeptidase (hSEP) inhibitory activity are protective in animal traumatic brain injury model. This property makes them useful for the preparation of pharmaceutical compositions for prophylaxis and treatment of neurodegenerative disorders.

The compounds of the invention are known from the European patents EP 0 733 642 EP 0 916 679 and EP 1 468 010, containing detailed syntheses, and can be described by the general formula (1):

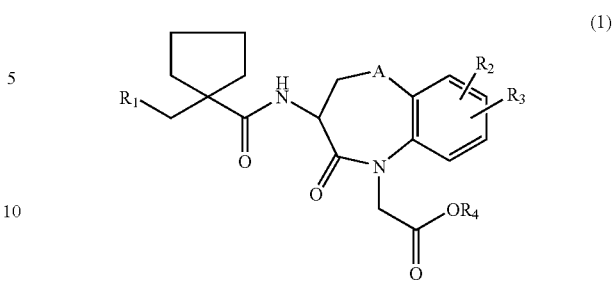

wherein:
$R_1$ stands for a group with formula (2) or (3):

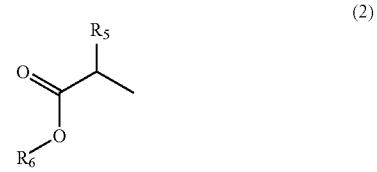

A represents $CH_2$, O or S,
$R_2$ and $R_3$ independently represent hydrogen or halogen,
$R_4$ and $R_6$ independently represent hydrogen or a biolabile carboxylic ester forming group;
$R_5$ is selected from the group consisting of $(C_1-C_6)$alkoxy $(C_1-C_6)$alkyl which may be substituted by a $(C_1-C_6)$ alkoxy, phenyl-$(C_1-C_6)$-alkyl and phenyloxy-$(C_1-C_6)$-alkyl wherein the phenylgroup may be substituted with $(C_1-C_6)$alkyl, $(C_1-C_6)$-alkoxy or halogen, and naphtyl-$(C_1-C6)$-alkyl,
$R_7$ and $R_8$ independently represent hydrogen or a group forming a biolabile phosphonic acid ester To the invention belong all compounds having formula (1), racemates, mixtures of diastereomers and the individual stereoisomers, and also include pharmacologically acceptable salts thereof. Thus compounds in which the substituents on potentially asymmetrical carbon atoms are in either the R-configuration or the S-configuration belong to the invention.

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277–280, 2004; P. Ettmayer et al., "Lessons learned from marketed and investigational prodrugs", J.Med.Chem., 47, 2393–2404, 2004). Pro-drugs, i.e. compounds which when administered to humans by any known route, are metabolised to compounds having formula (1), belong to the invention. In particular this relates to compounds with hydroxy groups. Such compounds can be reacted with organic acids to yield compounds having formula (1) wherein an additional group is present which is easily removed after administration, for instance, but not limited to amidine, enamine, a Mannich base, a hydroxylmethylene derivative, an O-(acyloxymethylene carbamate) derivative, carbamate, ester, amide or enaminone.

Pharmaceutically acceptable salts may be obtained using standard procedures well known in the art, for example by mixing a compound of the present invention with a suitable metal cation or an organic base, for instance an amine.

This objective can be achieved by preparing the metal salt of the compounds with the general formula (1) as mentioned above wherein the metal ion is a lithium ion or a bivalent metal ion. Preferred bivalent metal salts are calcium, magnesium and zinc salts. Most preferred is the calcium salt.

The invention particularly relates to compounds having general formula (4):

(4)

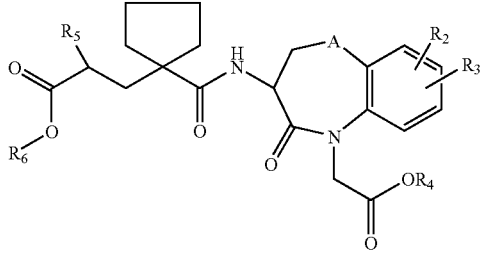

wherein the symbols have the meanings as given above.

More particular, the invention relates to compounds having general formula (5):

(5)

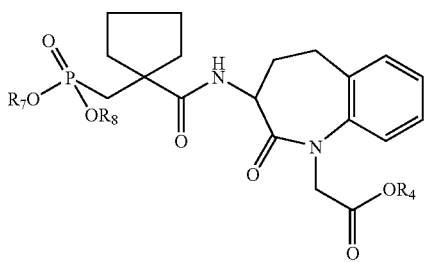

wherein the symbols have the meanings as given above.

The most preferred active substances according to the present invention are:

(2R)-2-{[1-({[(3S)-1-(carboxymethyl)-2-oxo-2,3,4,5-tetrahydro-1H-1-benzaepin-3-yl]amino}carbonyl)cyclopentyl]methyl}-4-phenylbutanoic acid (6):

(6)

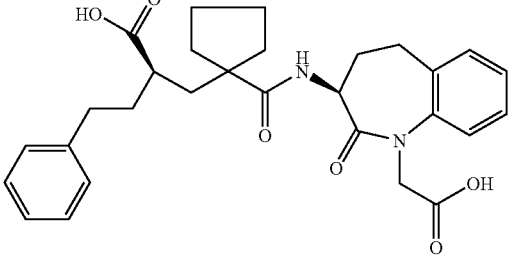

(2R)-2-{[1-({[(3S)-1-(carboxymethyl)-2-oxo-2,3,4,5-tetrahydro-1H-1-benzazepin-3-yl]amino)carbonyl)cyclopentyl]methyl}-4-(1-naphthyl)butanoic acid (7):

(7)

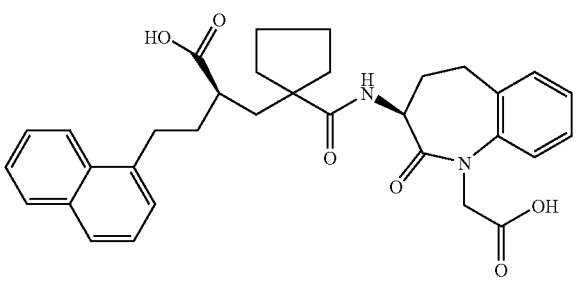

tert-butyl-((3S)-3-{[(1-{[(benzyloxy)(ethoxy)phosphoryl]methyl}cyclopentyl) carbonyl]amino}-2-oxo-2,3,4,5-tetrahydro-1H-1-benzazepin-1-yl)acetate (8):

(8)

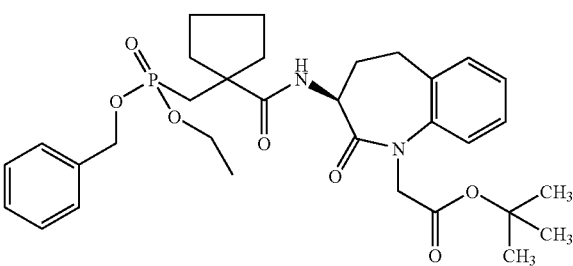

Pharmaceutical Compositions

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Very specific formulations suitable for the compounds of the invention have been described in the patent applications WO 03/068266 and WO 04/062692.

The specific compounds described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only, with a true scope and spirit of the invention being indicated by the claims.

Traumatic Brain Injury: Delayed Neuronal Death

Methods

Contusing device. The contusing device consisted of a stainless steel tube, 40 cm in length, perforated at 1 cm intervals to prevent air compression in the tube. Wistar rats, 230–270 g, were anesthetized with chloral hydrate, 400 mg/kg i.p., a craniotomy over the right hemisphere was made, the device guiding a falling weight onto the footplate resting upon the surface of the dura was placed perpendicular to the surface of the skull, and a force of 380 g×cm produced by a 20 g weight was selected to produce brain contusion. A maximum of 2.5 mm depression of the brain surface was allowed to avoid mechanical puncture of the dura. The center of the footplate was stereotaxically positioned 1.5 mm posterior and 2.5 mm lateral to the bregma. The rats underwent perfusion fixation 3 days after brain injury with a solution containing 4% paraformaldehyde in phosphate buffer.

Intracerebroventricular (i.c.v.) injections: Compounds were administered i.c.v. by means of a Hamilton syringe in a volume of 5–15 μl. Injections were performed over 5 min, 15 min–8 hrs after trauma using the following stereotaxic coordinates: AP=−0.5 mm, L=−2 mm and V=−5.5 in relation to bregma (Swanson, L. W. (1992) *Brain Maps: Structure of the Rat Brain*, Elsevier, Amsterdam).

Intravenous injections: Compounds were administered i.v. using a 1 ml syringe attached to a 26 gauge needle. The needle was inserted into the left femoral vein following a small skin incision. Compounds were administered in a volume of 1 ml/kg body weight over 30 sec.

Morphometric analysis in hippocampus. The damage in the hippocampal CA3 subfield was determined stereologically at 5 different rostrocaudal levels extending from 10.21 to 11.21 mm (Swanson, L. W. (1992) *Brain Maps: Structure of the Rat Brain*, Elsevier, Amsterdam) and throughout its mediolateral axis three days after traumatic injury. To quantitatively assess neuronal loss in the hippocampus, stereological disector technique (Cruz-Orive, L. M. & Weibel, E. R. (1990) *Am. J. Physiol.* 258, L148–L156) was used to estimate numerical density ($N_V$) of pyramidal neurons. An unbiased counting frame (0.05 mm×0.05 mm; disector height 0.01 mm) and a high-aperture objective (×40) were used for sampling. Normal neurons were identified by the presence of the typical nuclei with clear nucleoplasm and distinct nucleolus surrounded by cytoplasm containing Nissl substance. The border between CA2 and CA3 subfields was considered as the point where the looser arrangement of large pyramidal cells goes into densely packed pyramidal cells of the subfield CA3. An arbitrary line connecting the lateral ends of the dentate granule cell layers was considered a junction between subfields CA3 and CA4.

The compounds of the invention are useful in prophylaxis and treatment of neuro-degenerative disorders such as e.g. ischemic stroke, traumatic brain injury, acute disseminated encephalomyelitis, amyotrophic lateral sclerosis (ALS), retinitis pigmentosa, mild cognitive impairment, Alzheimer's disease, Pick's disease, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreichs ataxia, ataxia telangiectasia, epilepsy related brain damage, spinal cord injury, restless legs syndrome, Huntington's disease and Parkinson's disease, striatonigral degeneration, cerebral vasculitis, mitochondrial encephalo-myopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial or viral meningitis and meningoencephalitis, prion diseases, poisonings with neurotoxic compounds, Guillain Barre syndrome, chronic inflammatory neuropathies, polymyositis, dermatomyositis and radiation-induced brain damage.

The dosage expediently administered is 0.001–1000 mg/kg, preferably 0.1–100 mg/kg of patient's bodyweight.

Pharmacological Testresults

In the traumatic brain injury model described above, the compounds with the formulae 6 and 7 elicited dose-dependent neuroprotective effects. Those effects were still evident when the compounds with the formulae 6 and 7 were administered i.c.v. up to 8 hrs after trauma.

Dose Response of the Neuroprotective Effect of Test Compounds

Dose responses of the neuroprotective effect of the compounds with the formulae 6 and 7 when administered i.c.v. 15 min after trauma to adult Wistar rats were measured. Neuronal densities were determined in the CA3 hippocampal subfield as described in the methods. Densities of CA3 neurons±Standard Deviation (=SED) in 6 stereotactic levels in the left non-traumatized side of vehicle treated rats and the traumatized right side of vehicle treated rats and in rats treated with the compounds with the formulae 6 and 7 were measured and the results listed in table 1 below. In all of the following tables the numbers ("n") indicate the number of rats per group, where applicable.

TABLE 1

Neuronal densities CA3 hippocampus, cells × $10^3$/mm$^3$

| Stereo-tactic level | Vehicle left; (n = 8) | Vehicle right; (n = 8) | COMPOUND FORMULA (6) (N = 8) | COMPOUND FORMULA (7) (N = 8) |
|---|---|---|---|---|
| 10.21 | 148.57 ± 2.23 | 90.29 ± 5.54 | 112.5 ± 11.40 | 107.25 ± 15.19 |
| 10.41 | 154.29 ± 3.73 | 84.86 ± 7.29 | 103.75 ± 11.80 | 100.25 ± 14.71 |
| 10.61 | 158.86 ± 3.44 | 77.71 ± 5.82 | 101.75 ± 14.80 | 93.50 ± 16.96 |
| 10.81 | 155.71 ± 4.07 | 76.57 ± 13.45 | 98.50 ± 10.68 | 93.50 ± 12.36 |
| 11.01 | 150.86 ± 1.95 | 85.71 ± 10.98 | 96.75 ± 13.98 | 101.50 ± 18.81 |
| 11.21 | 148.29 ± 1.38 | 92.86 ± 8.71 | 101.75 ± 15.17 | 107.75 ± 16.51 |

Injection of vehicle into the right cerebral ventricle of rats subjected to head trauma resulted in the decrease of neuronal densities in the CA3 hippocampus up to 48% of control values, while injection of 10 µg of either the compound with the formula (6) or that with formula (7) partially prevented hippocampal neuronal loss. Analysis of variance ("ANOVA") revealed that there was a significant protective effect of treatment on neuronal loss in the CA3 hippocampus for both test substances.

Activity After Intravenous (i.v.) Administration

Injection of vehicle resulted in the decrease of neuronal densities in the CA3 hippocampus up to 53% of control values, while injection of 30 or 300 mg/kg of the test substance of formula (7) partially prevented hippocampal neuronal loss, with the dose of 300 mg/kg being most effective. Analysis of variance ("ANOVA") revealed that there was a significant protective effect of treatment on neuronal loss in the CA3 hippocampus for both tested doses of the test substance. (P<0.001; n=8 per group). ANOVA also revealed that the dose of 300 mg/kg conferred significantly better neuroprotection than the doses of 30 mg/kg.

TABLE 2

Neuronal densities CA3 hippocampus (cells × $10^3$/mm$^3$), i.v. administration

| Stereotactic level | Vehicle left; (n = 8) | Vehicle right; (n = 8) | COMPOUND FORMULA (7) 300 MG/KG (N = 8) | COMPOUND FORMULA (7) 30 MG/KG (N = 8) |
|---|---|---|---|---|
| 10.21 | 150.50 ± 1.41 | 97.50 ± 7.39 | 126.50 ± 5.53 | 107.50 ± 6.99 |
| 10.41 | 154.25 ± 1.67 | 90.25 ± 5.60 | 117.75 ± 4.95 | 102.25 ± 7.89 |
| 10.61 | 157.25 ± 2.38 | 84.75 ± 7.09 | 110.00 ± 7.01 | 100.75 ± 9.91 |
| 10.81 | 154.00 ± 1.85 | 88.00 ± 7.17 | 106.75 ± 7.48 | 101.75 ± 9.65 |
| 11.01 | 149.00 ± 1.07 | 94.00 ± 5.45 | 116.50 ± 9.06 | 111.25 ± 7.55 |
| 11.21 | 146.00 ± 1.51 | 99.75 ± 8.24 | 125.25 ± 5.01 | 117.75 ± 10.11 |

The invention claimed is:

1. A method of reducing neural loss in a patient in need thereof, comprising administering to the patient an effective amount of a pharmaceutical composition comprising at least one compound of the general formula (1):

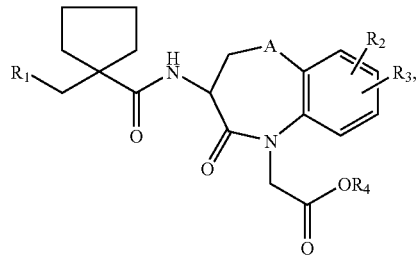

(1)

wherein:

$R_1$ is a group with formula (2) or (3):

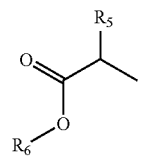

(2)

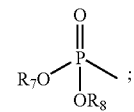

(3)

A is CH$_2$, O or S;

R$_2$ and R$_3$ independently are hydrogen or halogen;

R$_4$ and R$_6$ independently are hydrogen or a biolabile carboxylic ester forming group;

R$_5$ is selected from (C$_1$–C$_6$)alkoxy(C$_1$–C$_6$)alkyl which may be substituted by a (C$_1$–C$_6$)alkoxy, phenyl-(C$_1$–C$_6$)-alkyl and phenyloxy-(C$_1$–C$_6$)-alkyl wherein the phenylgroup may be substituted with (C$_1$–C$_6$)alkyl, (C$_1$–C$_6$)-alkoxy or halogen, and naphtyl-(C$_1$–C$_6$)-alkyl; and R$_7$ and R$_8$ independently are hydrogen or a group forming a biolabile phosphonic acid ester;

or a stereoisomer, pharmacologically acceptable salt, or prodrugs thereof.

2. The method of claim 1, wherein the at least one compound of the general formula (1) is a compound of the general formula (4):

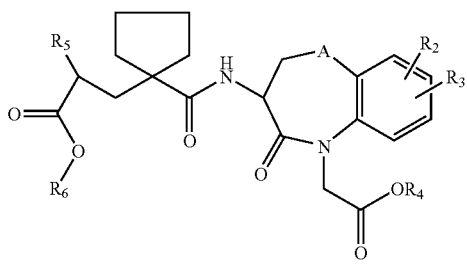

(4)

3. The method of claim 1, wherein the at least one compound of the general formula (1) is a compound of the general formula (5):

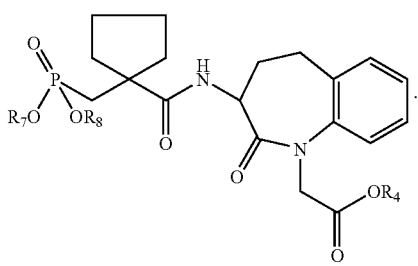

(5)

4. The method of claim 1, wherein the at least one compound of the general formula (1) is (2R)-2-{[1-({[(3S)-1-(carboxymethyl)-2-oxo-2,3,4,5-tetrahydro-1H-1-benzazepin-3-yl] amino}carbonyl)cyclopentyl] methyl}-4-phenylbutanoic acid having formula (6):

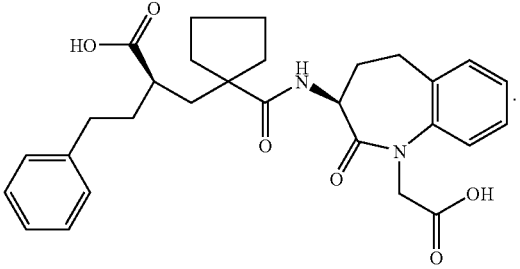

(6)

5. The method of claim 1, wherein the at least one compound of the general formula (1) is (2R)-2-{[1-({[(3S)-1-(carboxymethyl )-2-oxo-2,3,4,5-tetrahydro-1H-1-benzazepin-3-yl]amino}carbonyl)cyclopentyl] methyl}-4-(1-naphthyl )butanoic acid, having formula (7):

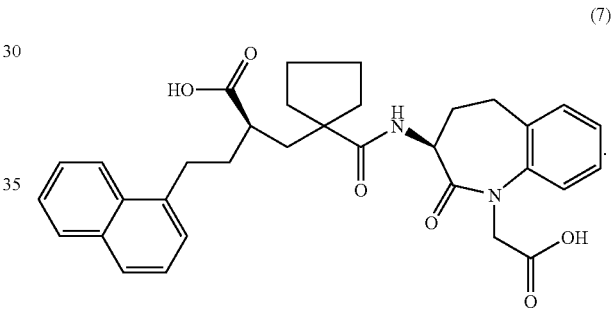

(7)

6. The method of claim 1, wherein the at least one compound of the general formula (1) is tert-butyl-((3S)-3-{[(1-{[(benzyloxy)(ethoxy)phosphoryl] methyl}cyclopentyl) carbonyl]amino}-2-oxo-2,3,4,5-tetrahydro-1H-1-benzazepin-1-yl)acetate, having formula (8):

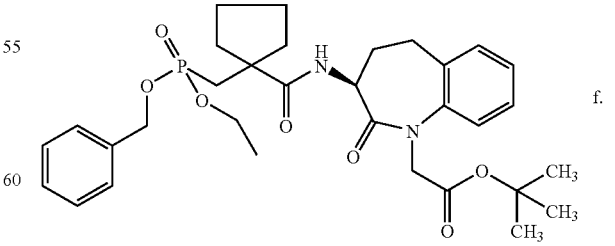

(8)

7. The method of claim 1, wherein the pharmacologically acceptable salt is a lithium salt, calcium salt, magnesium salt or zinc salt.

8. The method of claim 1, wherein the neural loss is associated with one or more of traumatic brain injury, acute disseminated encephalo-myelitis, epilepsy related brain damage, spinal cord injury, bacterial or viral meningitis and meningo-encephalitis, prion diseases, poisonings with neurotoxic compounds, radiation-induced brain damage, and ischemic stroke.

9. The method of claim 8, wherein neural loss associated with at least one of traumatic brain injury and spinal cord injury is reduced.

10. The method of claim 8, wherein neural loss associated with at least one of acute disseminated encephalo-myelitis, epilepsy related brain damage, bacterial or viral meningitis and meningoencephalitis, prion diseases, poisonings with neurotoxic compounds, and radiation-induced brain damage is reduced.

11. The method of claim 8, wherein neural loss associated with ischemic stroke is reduced.

* * * * *